US007943805B2

(12) United States Patent
Suppes et al.

(10) Patent No.: US 7,943,805 B2
(45) Date of Patent: May 17, 2011

(54) METHOD OF PRODUCING LOWER ALCOHOLS FROM GLYCEROL

(75) Inventors: Galen J. Suppes, Columbia, MO (US); William Rusty Sutterlin, Columbia, MO (US); Mohanprasad Dasari, Columbia, MO (US)

(73) Assignee: The Curators Of The University Of Missouri, Columbia, MO (US)

( * ) Notice: Subject to any disclaimer, the term of this patent is extended or adjusted under 35 U.S.C. 154(b) by 0 days.

(21) Appl. No.: 12/906,358

(22) Filed: Oct. 18, 2010

(65) Prior Publication Data

US 2011/0040132 A1 Feb. 17, 2011

Related U.S. Application Data

(60) Division of application No. 12/645,213, filed on Dec. 22, 2009, now Pat. No. 7,816,567, which is a division of application No. 11/088,603, filed on Mar. 24, 2005, now Pat. No. 7,663,004, and a continuation-in-part of application No. 10/420,047, filed on Apr. 21, 2003, now abandoned.

(60) Provisional application No. 60/556,334, filed on Mar. 25, 2004, provisional application No. 60/374,292, filed on Apr. 22, 2002, provisional application No. 60/410,324, filed on Sep. 13, 2002.

(51) Int. Cl.
*C07C 29/132* (2006.01)
(52) U.S. Cl. .................................. 568/861
(58) Field of Classification Search .................. 568/861
See application file for complete search history.

(56) References Cited

U.S. PATENT DOCUMENTS

| 3,871,445 | A | 3/1975 | Wanka et al. |
| 4,516,632 | A | 5/1985 | Swift et al. |
| 4,642,394 | A | 2/1987 | Che |
| 5,214,219 | A | 5/1993 | Casale et al. |
| 5,266,181 | A | 11/1993 | Matsumura et al. |
| 5,276,181 | A | 1/1994 | Casale et al. |
| 5,616,817 | A | 4/1997 | Schuster et al. |
| 5,811,597 | A | 9/1998 | Hwan et al. |
| 6,080,898 | A | 6/2000 | Drent et al. |
| 6,488,742 | B1 | 12/2002 | Grunewald et al. |
| 2002/0077501 | A1 | 6/2002 | Hoyme et al. |
| 2005/0244312 | A1 | 11/2005 | Suppes et al. |
| 2007/0287865 | A1 | 12/2007 | Arredondo et al. |

FOREIGN PATENT DOCUMENTS

| DE | 524 1001 C | 5/1931 |
| DE | 41 28 692 A1 | 3/1993 |
| DE | 4302464 A1 | 8/1994 |
| EP | 0523 015 A | 1/1993 |
| EP | 0523014 A2 | 1/1993 |
| EP | 0544 157 A | 6/1993 |
| EP | 0713849 A1 | 5/1996 |
| EP | 0 826 691 A | 3/1998 |
| GB | 490 211 A | 8/1938 |
| JP | 2002 265986 A | 9/2002 |
| WO | WO 9305006 | 3/1993 |
| WO | WO 01/46102 A | 6/2001 |
| WO | WO 01/66499 A | 9/2001 |
| WO | WO 03/087041 A | 10/2003 |
| WO | WO2005/095536 A2 | 10/2005 |
| WO | WO 2007053705 | 10/2007 |

OTHER PUBLICATIONS

PCT/US2008/087842 International Search Report & Written Opinion mailed Mar. 5, 2009, 14 pages.
European Application No. 05726117; Examination Report dated Apr. 16, 2007; 3 pages.
European Application No. 05726117; Response to Examination Report dated Oct. 26, 2007; 5 pages.
Itsuno, Organic Reactions, 1998, 52 (Bib. And Reaction equation 522 of 659).
PCT/US06/042707 International Search Report and Written Opinion; mailed Apr. 7, 2007; 16 pages.
PCT/US05/009901 International Preliminary Report on Patentability, Sep. 26, 2006; 21 pages.
U.S. Appl. No. 10/420,047; Restriction Requirement mailed Jan. 2, 2004; 4 pages.
U.S. Appl. No. 10/420,047; Response to Restriction Requirement filed Jan. 29, 2004; 2 pages.
U.S. Appl. No. 10/420,047; Office Action mailed May 19, 2004; 9 pages.
U.S. Appl. No. 10/420,047; Response to Office Action filed Aug. 3, 2004; 3 pages.
International Search Report and Written Opinion for PCT/US2005/009901, Jan. 19, 2006.
Dasari, M.A., et al.: "Low-Pressure Hydrogenolysis Of Glycerol To Propylene Glycol," Applied Catalysis A: General, Elsevier Science, Amsterdam, Netherlands, vol. 281, No. 1-2, p. 225-231, Jan. 1, 2005.
Montassier, C., et al.: "Deactivation Of Supported Copper Based Catalysts During Polyol Conversion In Aqueous Phase" Applied Catalysis A: General, Elsevier Science, Amsterdam, Netherlands, vol. 121, No. 2, p. 231-244, Jan. 19, 1995.
Montassier, C., et al.: "Polyol Conversion by Liquid Phase Heterogeneous Catalysis Over Metals," Heterogeneous Catalysis And Fine Chemicals, p. 165-170, 1988.
U.S. Appl. No. 12/645,213, Notice of Allowance mailed Jun. 14, 2010, 6 pages.
European Application No. 06836781.2, Communication Pursuant to Article 94(3) EPC dated Apr. 20, 2010, 8 pages.
European Application No. 05726117.4, Communication Pursuant to Article 94(3) EPC dated Jan. 12, 2010, 5 pages.
European Application No. 05726117.4, Response to Communication filed Jul. 22, 2010, 15 pages.

(Continued)

*Primary Examiner* — Elvis O Price
(74) *Attorney, Agent, or Firm* — Lathrop & Gage LLP

(57) ABSTRACT

A reactive-separation process converts glycerin into lower alcohols, having boiling points less than 200° C., at high yields. Conversion of natural glycerin to propylene glycol through an acetol intermediate is achieved at temperatures from 150° to 250° C. at a pressure ranging from 1 and 25 bar. The preferred applications of the propylene glycol are as an antifreeze, deicing compound, or anti-icing compound. The preferred catalyst for this process in a copper-chromium powder.

13 Claims, 3 Drawing Sheets

OTHER PUBLICATIONS

U.S. Appl. No. 11/510,992, Restriction Requirement mailed Mar. 15, 2010, 6 pages.

U.S. Appl. No. 11/510,992, Restriction Requirement filed Apr. 15, 2010, 14 pages.

U.S. Appl. No. 11/510,992, Notice of noncompliant response mailed Apr. 29, 2010, 2 pages.

U.S. Appl. No. 11/510,992, Response to Notice of noncompliant response filed Apr. 29, 2010, 14 pages.

U.S. Appl. No. 11/510,992, Office Action mailed Jul. 22, 2010, 5 pages.

U.S. Appl. No. 11/088,603, Examiner Interview Summary and Notice of Allowance dated Sep. 29, 2009, 7 pages.

U.S. Appl. No. 11/088,603 Office Action mailed Jul. 24, 2008; 10 pages.

U.S. Appl. No. 11/088,603 Response to Office Action filed Oct. 24, 2008; 12 pages.

U.S. Appl. No. 11/088,603 Office Action mailed Feb. 18, 2009; 8 pages.

U.S. Appl. No. 11/088,603 Response to Office Action filed Aug. 18, 2009; 15 pages.

European Application No. 06836781.2; Response dated Oct. 28, 2010, 24 pages.

U.S. Appl. No. 11/510,992, Response to Office Action filed Jan. 21, 2011, 16 pages.

European Application No. 06 836 781.2, Response to Office Action filed Oct. 28, 2010, 6 pages.

European Application No. 06 836 781.2, Summons to attend oral proceedings, Dec. 27, 2010, 8 pages.

METHOD OF PRODUCING LOWER ALCOHOLS FROM GLYCEROL

RELATED APPLICATIONS

This application is a Divisional application of U.S. patent application Ser. No. 12/645,213 filed Dec. 22, 2009 now U.S. Pat. No. 7,816,567, which is a Divisional of U.S. patent application Ser. No. 11/088,603 filed Mar. 24, 2005 (now U.S. Pat. No. 7,663,004), which claims benefit of priority to U.S. provisional patent application Ser. No. 60/556,334 filed Mar. 25, 2004 and is a continuation-in-part of U.S. patent application Ser. No. 10/420,047 filed Apr. 21, 2003 now abandoned, which claims benefit of priority to U.S. provisional Patent Application Ser. Nos. 60/374,292, filed Apr. 22, 2002 and 60/410,324, filed Sep. 13, 2002, all of which are incorporated by reference herein.

BACKGROUND

1. Field of the Invention

This invention relates generally to a process for value-added processing of fats and oils to yield glycerol and glycerol derivatives. More particularly, the process converts glycerol to acetol and/or propylene glycol, which is also known as 1,2 propanediol. The process may yield glycerol-based products and glycerol derivatives, such as antifreeze and other products.

2. Description of the Related Art

Conventional processing of natural glycerol to propanediols uses a catalyst, for example, as reported in U.S. Pat. Nos. 5,616,817, 4,642,394, 5,214,219 and U.S. Pat. No. 5,276,181. These patents report the successful hydrogenation of glycerol to form propanediols. None of the processes shown by these patents provide a direct reaction product mixture that is suitable for use as antifreeze. None provide process conditions and reactions that suitably optimize the resultant reaction product mixture for direct use as antifreeze. None address the use of unrefined crude natural glycerol feed stock, and none of these processes are based on reactive distillation.

U.S. Pat. No. 5,616,817 issued to Schuster et al. describes the catalytic hydrogenation of glycerol to produce propylene glycol in high yield, such as a 92% yield, with associated formation of n-propanol and lower alcohols. Conversion of glycerol is substantially complete using a mixed catalyst of cobalt, copper, manganese, and molybdenum. Hydrogenation conditions include a pressure of from 100 to 700 bar and a temperature ranging from 180° C. to 270° C. Preferred process conditions include a pressure of from 200 to 325 bar and a temperature of from 200° C. to 250° C. The lower pressures lead to incomplete reactions and the higher pressures increasingly form short chain alcohols. A crude glycerol feed may be used, such as is obtainable from the transesterification of fats and oils, but needs to be refined by short path distillation to remove contaminants, such as sulfuric acid that is commonly utilized in the transesterification process. The feed should contain glycerol in high purity with not more than 20% water by weight.

U.S. Pat. No. 4,642,394 issued to Che et al. describes a process for catalytic hydrogenation of glycerol using a catalyst that contains tungsten and a Group VIII metal. Process conditions include a pressure ranging from 100 psi to 15,000 psi and a temperature ranging from 75° C. to 250° C. Preferred process conditions include a temperature ranging from 100° C. to 200° C. and a pressure ranging from 200 to 10,000 psi. The reaction uses basic reaction conditions, such as may be provided by an amine or amide solvent, a metal hydroxide, a metal carbonate, or a quaternary ammonium compound. The concentration of solvent may be from 5 to 100 ml solvent per gram of glycerol. Carbon monoxide is used to stabilize and activate the catalyst. The working examples show that process yields may be altered by using different catalysts, for example, where the yield of propanediols may be adjusted from 0% to 36% based upon the reported weight of glycerol reagent.

U.S. Pat. Nos. 5,214,219 issued to Casale, et al. and 5,266,181 issued to Matsumura, et al. describe the catalytic hydrogenation of glycerol using a copper/zinc catalyst. Process conditions include a pressure ranging from 5 MPa to 20 MPa and a temperature greater than 200° C. Preferred process conditions include a pressure ranging from 10 to 15 MPa and a temperature ranging from 220° C. to 280° C. The concentration of glycerol may range from 20% to 60% by weight in water or alcohol, and this is preferably from 30% to 40% by weight. The reaction may be adjusted to produce significant amounts of hydrocarbon gas and/or lactic acid, such that gas generation is high when lactic acid formation is low and lactic acid formation is high when gas generation is low. This difference is a function of the amount of base, i.e., sodium hydroxide, which is added to the solvent. Alcohol reaction products may range from 0% to 13% of hydrocarbon products in the reaction mixture by molar percentages, and propanediols from 27% to 80%. Glycerol conversion efficiency ranges from 6% to 100%.

SUMMARY

The presently disclosed process advances the art and overcomes the problems outlined above by producing value-added products, such as antifreeze; from hydrogenation of natural glycerol feed stocks.

In one aspect, the process yields a glycerol-derived antifreeze composition that may be mixed with water for use as a radiator fluid for vehicles or as a heat exchange fluid in a building. In another aspect, a propylene glycol-based antifreeze or deicing composition may also be produced by the process disclosed herein, where the propylene-glycol-based antifreeze is produced from a natural glycerol feed stock.

In one embodiment, the process is used to convert glycerol to propylene glycol with high selectivity. A glycerol-containing feedstock that contains 50% or less by weight water is combined with a catalyst that is capable of hydrogenating glycerol. The reaction mixture is heated to a temperature ranging from 150° to 250° C. over a reaction time interval ranging from 2 to 96 hours at a pressure ranging from 1 and 25 bar. The feedstock more preferably contains from 5% to 15% water by weight. The catalyst is preferably a heterogeneous catalyst, such as palladium, nickel, rhodium, copper, zinc, chromium and combinations thereof.

Reaction product vapors may be removed or separated from the reaction mixture during the step of heating. Where the reaction is limited by an absence of hydrogen, an acetol and/or lactaldehyde product is formed. These reaction products may be hydrogenated in a further reaction step to produce propylene glycol. Alternatively, the reaction to convert glycerol into acetol proceeds simultaneously with hydrogenation when sufficient hydrogen is present.

Particularly preferred glycerol-containing feedstocks include those that are produced from bio-renewable resources, such as vegetable oils and especially soy oil. The feedstock may, for example, be provided as the crude glycerol byproduct of a $C_1$ to $C_4$ alkyl alcohol alcoholysis of a glyceride. In such cases, the reaction products of the disclosed process may be provided for direct use as an antifreeze, deicing agent, or anti-icing agent, or the reaction products may be blended with other materials for such use. A typical product of this nature may contain on a water-free basis from about 0.5% to about 60% glycerol, and from about 20% to about 85% propylene glycol. Other products may contain on a water-free basis from about 10% to about 35% glycerol, from about 40% to about 75% propylene glycol, and from about 0.2% to about 10% $C_1$ to $C_4$ alkyl alcohol. Depending upon the nature of the feedstock, there may also be present from about 1% to 15% by weight of a residue by-product from the reaction to convert the glycerol.

One process for producing antifreeze from a crude glycerol byproduct of a $C_1$ to $C_4$ alkyl alcohol alcoholysis of a glyceride commences with a step of neutralizing the crude glycerol feedstock to achieve a pH between 5 and 12. The $C_1$ to $C_4$ alcohol and water are separated from the crude glycerol feedstock such that the combined concentrations of water and $C_1$ to $C_4$ alcohols is less than about 5 (wt) %. The separated crude glycerol feed is contacted with a hydrogenation catalyst and hydrogen at a pressure of between about 1 and 200 bar and at a temperature between about 100° C. and 290° C. for a period of time sufficient to achieve a conversion of the glycerol of between 60 and 90%. The contacting pressure usually ranges from 1 to 20 bar.

The process for converting glycerol to propylene glycol may be interrupted by limiting or eliminating the hydrogen reagent. This results in the production of acetol and/or lactaldehyde. These products may be provided as a feedstock for a further catalyzed reaction with hydrogen to complete the conversion to propylene glycol. The process of converting acetol or lactaldehyde to propylene glycol has high selectivity. An acetol or lactaldehyde-containing feedstock with less than 50% by weight water is combined with a catalyst that is capable of hydrogenating acetol and/or lactaldehyde to form a reaction mixture. The reaction mixture is heated to a temperature ranging from 50° to 250° C. over a reaction time interval ranging from 0 to 24 hours at a pressure ranging from 1 and 25 bar. The reaction time is preferably greater than 0.5 hours. In some embodiments, the acetol or lactaldehyde-containing feedstock used in the step of combining may contain from 0% to 35% water in acetol by weight. The catalyst used in the step of combining may be a heterogeneous catalyst selected from the group consisting of palladium, nickel, rhodium, copper, zinc, chromium and combinations thereof. The temperature used in the heating step preferably ranges from 150° C. to 220° C. The pressure used in the heating step preferably ranges from 10 to 20 bar.

DETAILED DESCRIPTION OF PREFERRED EMBODIMENTS

There will now be shown and described by way of non-limiting example a process for producing lower alcohols from glycerol feed stock to provide glycerol-based and/or propylene glycol-based antifreezes. The lower alcohols include, for example, as acetol and propylene glycol. Preferred uses of reaction product mixtures that are derived from the process include but are not limited to deicing fluids, anti-icing fluids, and antifreeze applications. These uses of the glycerol-based and/or propylene glycol-based antifreezes displace the use of toxic and non-renewable ethylene glycol with non-toxic and renewable glycerol-derived antifreeze. In this regard, use of propylene glycol that is derived from natural glycerol is a renewable alternative to petroleum-derived propylene glycol. Other downstream uses for propylene glycol include any substitution or replacement of ethylene glycol or glycerol with propylene glycol.

Equipment for Reactive-Separation Preparation of Antifreeze from Poly-Alcohols Like Glycerol One method of preparing antifreeze from glycerol includes reaction at a temperature ranging from 150° to 250° C. and in some embodiments this temperature is more preferably from 180° C. to 220° C. The reaction occurs in a reaction vessel. The pressures in the reaction vessel are preferably from 1 to 25 atmospheres (or from 1 to 25 bar) and in some embodiments this pressure is more-preferably between 5 and 18 atmospheres. The process equipment may include, for example, a reactor at these temperature and pressure conditions connected to a condenser and condensate tank where the condenser is preferably at a temperature between about 25° C. and 150° C. and in some embodiments this is more preferably between 25° and 60° C.

Figure 1:
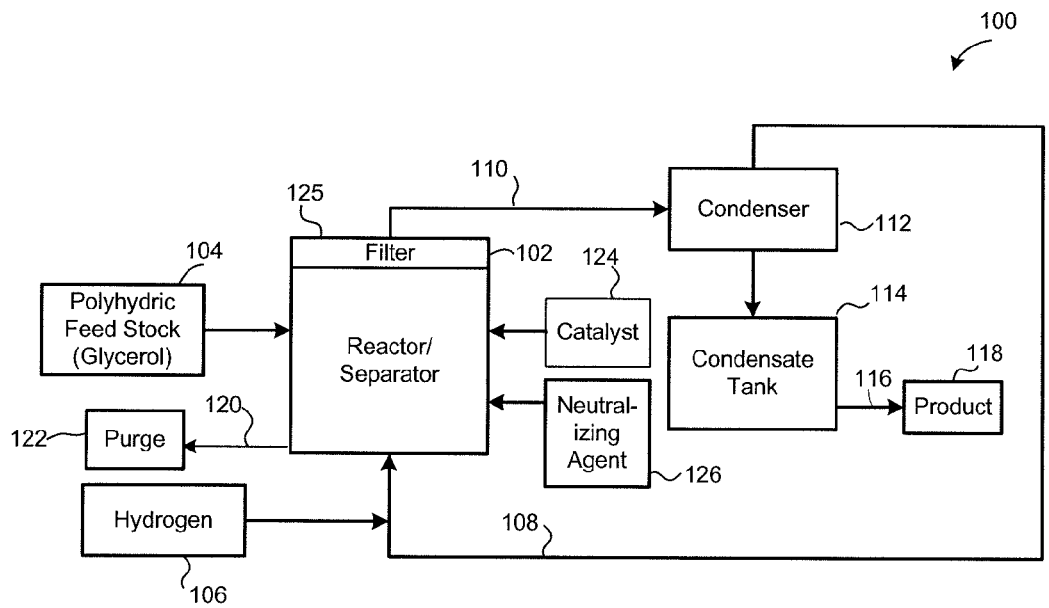
FIG. 1 is a schematic block flow diagram illustrating preferred reactor-separator with a reactor, condenser, and condensate tank, and recycle of unreacted hydrogen.

FIG. 1 provides a block flow diagram of process equipment 100 including a reactor-separator 102. A polyhydric feed stock 104, for example, containing glycerol, is introduced stepwise or continuously into the reactor separator 102. Hydrogen 106 is added to hydrogen line 108 to promote conversion of glycerol 104 to propylene glycol within the reactor-separator 102. The process temperatures are such that a distillation occurs with the formation or presence of propylene glycol, short chain alcohols, and water, which vaporize and flow through overhead line 110 to a condenser 112. Most of the alcohol, water and propylene glycol vapors condense in the condenser 112 and are collected in the condensate tank 114 for discharge through discharge line 116 as product 118. Unreacted hydrogen and remaining vapors from the condenser 112 are recycled back to the reactor-separator 102 through the hydrogen recycle line 108.

Reaction products 118 are removed from the condensate tank 112 through discharge line 116, and the reaction mixture inside reactor-separator 102 may be purged periodically or at a slow flow rate through purge line 120 to obtain purge mixture 122. Purging is necessary or desirable when non-volatile reaction by-products are formed and when metals or inorganic acids, such as residual biodiesel catalysts, are present in the polyhydric feed stock 104. Catalysts and useful components, such as glycerol and propylene glycol, are preferably recovered from the purge mixture 122.

The reaction inside reactor-separator 102 is catalyzed, and may be facilitated at periodic intervals or by the continuous introduction of a suitable catalyst 124, which may be any catalyst that is suitable for use in converting glycerol into lower alcohols, such as acetol and/or propylene glycol. The catalyst 124 may reside within the reactor-separator as a packed bed, or distribution of the catalyst 124 inside reactor-separator 102 may be improved by using the hydrogen gas 108 to provide a fluidized bed, or by stirring (not shown). Agitated slurry reactors of a liquid phase reaction with a vapor overhead product are preferred. The catalyst 124 is mixed with the polyhydric feedstock 104 that is undergoing reaction in the reactor separator 102 to facilitate breaking of carbon-oxygen or carbon-carbon bonds including but not limited to hydrogenation. As used herein, hydrogenolysis and hydrogenation are interchangeable terms. By way of example the reaction of glycerol with hydrogen to form propylene glycol and water is referred to frequently as hydrogenation in this text. Suitable catalysts for this purpose may include, without limitation, such metals as platinum, palladium, ruthenium, chromium, nickel, copper, zinc, rhodium, chromium, ruthenium, and combinations thereof. Catalysts may be deposited on a substrate, such as an alumina substrate. The best catalysts are non-volatile, and are preferably prevented from exiting the reactor separator 102 into the condensate tank 114. A filter 125 in the overhead discharge line 110 from the reactor separator 102 retains solid catalysts in the reactor separator 102. No limitations are placed or implied on whether the catalyst is soluble or solid, the oxidative state of the catalyst, or the use of solid supports or soluble chelates.

Reaction times at preferred conditions may range from 2 hours to 96 hours, and this is more preferably from 4 to 28 hours. Reaction time may be defined as the volume of liquid in the reactor divided by the time-averaged flow rate of liquids into the reactor. While the preferred reaction times are greater than 2 hours, the average residence time at higher loadings of catalyst 124 can be less than an hour and typically longer than 0.5 hours. While preferred temperatures are up to 250° C., the reactor-separator may be operated at temperatures up to 270° C. with satisfactory results.

The polyhydric feed stock 104 preferably contains glycerol. In a broader sense, polyhydric feedstock 104 may contain, for example, from 5% to substantially 100% of a polyol, for example, glycerol, sorbitol, 6-carbon sugars, 12-carbon sugars, starches and/or cellulose.

As illustrated in FIG. 1, the process equipment 100 is preferably configured to provide hydrogen 106 as a reagent; however, the use of hydrogen is optional. Commercially valuable products may be formed as intermediates that collect in the condensate tank in the absence of hydrogen. Accordingly, use of hydrogen 106 is preferred, but not necessary. For example, the intermediates collecting in condensate tank 114 may include acetol (hydroxy-2-propanone), which may be subjected to hydrogenolysis in another process, which is shown below in FIG. 3. In addition to reagents, the material within reactor separator 102 may contain water, salts, or catalysts residue from previous processes.

One type of polyhydric feedstock 104 may contain glycerol that is prepared by transesterification of oils or fatty acids, for example, as described in co-pending application Ser. No. 10/420,047 filed Apr. 23, 2003, which is incorporated by reference to the same extent as though fully replicated herein. In a polyhydric feedstock 104 of this type, water may be present in an amount ranging from 0% to 70%. More preferably, water is present in an amount ranging from 5% to 15%. Water may be added to reduce side-reactions, such as the formation of oligomers.

One advantage of using the process equipment 100 is that volatile alcohol products are removed from the reaction mixture as they are formed inside reactor separator 102. The possibility of degrading these products by continuing exposure to the reaction conditions is commensurately decreased by virtue of this removal. In addition, the volatile reaction products are inherently removed from the catalysts to provide relatively clean products. This reaction-separation technique is especially advantageous for catalysts that are soluble with or emulsified in the reaction mixture.

A preferred class of catalyst 124 is the copper chromite catalyst, $(CuO)_x(Cr_2O_3)y$. This type of catalyst is useful in the process and is generally available commercially. In this class of catalyst, the nominal compositions of copper expressed as CuO and chromium expressed as $Cr_2O_3$ may vary from about 30-80 wt % of CuO and 20-60 wt % of $Cr_2O_3$. Catalyst compositions containing about 40-60 wt % copper and 40-50 wt % of chromium are preferred.

Preferred catalysts for use as catalyst 124, in addition to the copper and chromium previously described, also include barium oxide and manganese oxide or any of their combinations. Use of barium and manganese is known to increase the stability of the catalyst, i.e., the effective catalyst life. The nominal compositions for barium expressed as barium oxide can vary 0-20 wt % and that for manganese expressed as manganese oxide can vary from 0-10 wt %. The most preferred catalyst compositions comprise from 40%-60 wt % of CuO 40-55 wt % of $Cr_2O_3$, 0-10 wt % of barium oxide and 0-5 wt % manganese oxide.

Reaction Mechanism

According to one mechanism proposed by Montassier et al. (1988), dehydrogenation of glycerol on copper can form glyceric aldehyde in equilibrium with its enolic tautomer. The formation of propylene glycol was explained by a nucleophilic reaction of water or adsorbed OH species, a dehydroxylation reaction, followed by hydrogenation of the intermediate unsaturated aldehyde. This reaction mechanism was observed not to apply in our investigation.

Figure 2:
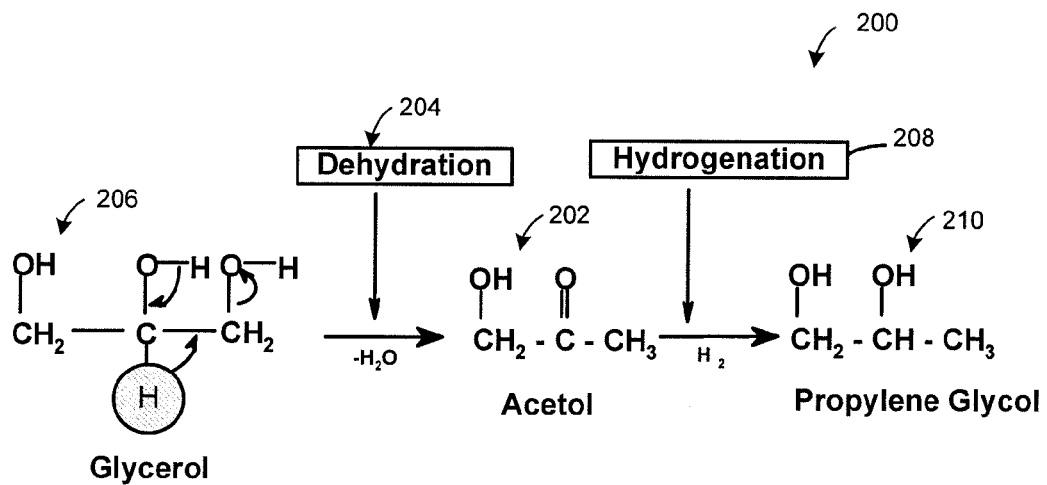
FIG. 2 is a schematic of the proposed reaction mechanism for conversion of glycerol to propylene glycol via acetol intermediate.

FIG. 2 shows a preferred reaction mechanism 200 for use in the reactor-separator 102 of FIG. 1, and for which process conditions may be suitably adjusted as described above. As shown in FIG. 2, hydroxyacetone (acetol) 202 is formed, and this is possibly an intermediate of an alternative path for forming propylene glycol by a different mechanism. The acetol 202 is formed by dehydration 204 of a glycerol molecule 206 that undergoes intramolecular rearrangements as shown. In a subsequent hydrogenation step 208, the acetol 202 further reacts with hydrogen to form propylene glycol 210 with one mole of water by-product resulting from the dehydration step 204.

Early studies to investigate the effect of water on the hydrogenolysis reaction indicated that the reaction takes place even in absence of water with a 49.7% yield of propylene glycol. Moreover, and by way of example, the reaction is facilitated by use of a copper-chromite catalyst, which may be reduced in a stream of hydrogen prior to the reaction. In this case, the incidence of surface hydroxyl species taking part in the reaction is eliminated. The above observations contradict the mechanism proposed by Montassier et al. where water is present in the form of surface hydroxyl species or as a part of reactants.

EXAMPLE 1

Confirmation of Reaction Mechanism

An experiment was performed to validate the reaction mechanism 200. Reactions were conducted in two steps, namely, Steps 1 and 2. In step 1, relatively pure acetol was isolated from glycerol. Temperature ranged from 150° C. to 250° C. and more specifically from 180° C. to 220° C. There was an absence of hydrogen. Pressure ranged from 1 to 14 psi (6.9 MPa to 96 MPa) more specifically from 5 to 10 psi (34 MPa to 69 MPa). A copper-chromite catalyst was present. In Step 2, the acetol formed in Step 1 was further reacted in presence of hydrogen to form propylene glycol at a temperature ranging from 150° C. to 250° C. and more preferably between 180 to 220° C. Excess hydrogen was added at a hydrogen over pressure between 1 to 25 bars using the same catalyst.

Figure 3:
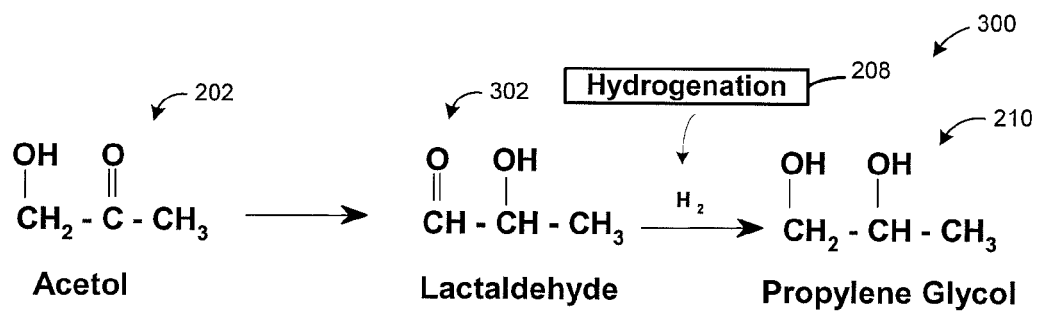
FIG. 3 is a schematic of the proposed two-step alternative embodiment for converting glycerol to acetol and then converting acetol to propylene glycol.

It was observed in the Step 2 of converting acetol to propylene glycol that lactaldehyde was formed. Propylene glycol is also formed by the hydrogenation 208 of lactaldehyde 302, as illustrated in FIG. 3. With respect to FIG. 2, lactaldehyde represents an alternative path for forming propylene glycol from acetol. FIG. 3 shows this mechanism 300 where the acetol undergoes a rearrangement of the oxygen double bond to form lactaldehyde 302, but the dehydrogenation step 208 acting upon the lactaldehyde 302 also results in the formation of propylene glycol 210. It was also observed that the formation of lactaldehyde intermediate was predominant at lower reaction temperatures in the range of from 50° C. to 150° C. (see Example 8 below).

This and subsequent reactions were performed in liquid phases with catalyst and sufficient agitation to create a slurry reaction mixture.

EXAMPLE 2

Simultaneous Dehydration and Hydrogenation Using Various Catalysts and Reagent Mixtures A variety of reaction procedures were performed to show that reaction efficiency may be optimized at any process conditions, such as reaction time, temperature, pressure and flash condition by the selection or choice of catalyst for a given polyhydric feedstock.

Table 1 reports the results of reacting glycerol in the presence of hydrogen and catalyst to form a mixture containing propylene glycol. The reaction vessel contained 80 grams of refined glycerol, 20 grams of water, 10 grams of catalyst, and a hydrogen overpressure of 200 psig. The reactor was a closed reactor that was topped off with excess hydrogen. The reaction occurred for 24 hours at a temperature of 200° C. All catalysts used in this Example were purchased on commercial order and used in the condition in which they arrived.

TABLE 1

Summary of catalyst performances based on 80 grams of glycerol reported on a 100 grams basis.

|  | Initial Loading (g) | Best Possible (g) | Catalyst 5% Ruthenium on carbon (g) | Catalyst Raney-Copper (g) | Catalyst Raney-Nickel (g) |
| --- | --- | --- | --- | --- | --- |
| Glycerol | 100 | 0 | 63.2 | 20.6 | 53.6 |
| Water | 25 | 43 | not measured | not measured | not measured |

TABLE 1-continued

Summary of catalyst performances based on 80 grams of glycerol reported on a 100 grams basis.

|  | Initial Loading (g) | Best Possible (g) | Catalyst 5% Ruthenium on carbon (g) | Catalyst Raney-Copper (g) | Catalyst Raney-Nickel (g) |
| --- | --- | --- | --- | --- | --- |
| Propylene Glycol | 0 | 82 | 14.9 | 27.5 | 14.9 |
| Ethylene Glycol | 0 | 0 | 16.9 | 13.1 | 16.5 |
| Acetol | 0 | 0 | 0.0 | 12.1 | 0.0 |
| Total, excluding water | 100 | 82 | 94.9 | 73.2 | 85.0 |

Table 2 summarizes reaction performance with a higher initial water content, namely, 30 grams of refined glycerol and 70 grams of water. The reactions were conducted at the following initial conditions: 5% wt of catalyst, and a hydrogen overpressure of 1400 kPa. The following table presents compositions after reacting in a closed reactor (with topping off of hydrogen) for 24 hours at a reaction temperature of 200° C.

TABLE 2

Summary of catalyst performances based on 30 grams initial loading of glycerol and 70 grams of water.

|  | Initial Loading (g) | Best Possible (g) | Catalyst 5% Ruthenium on carbon (g) | Catalyst Raney-Copper (g) | Catalyst Raney-Nickel (g) |
| --- | --- | --- | --- | --- | --- |
| Glycerol | 30 | 0 | 20.8 | 19.1 | 3.8 |
| Propylene Glycol | 0 | 24 | 9.3 | 7.23 | 3.1 |
| Ethylene Glycol | 0 | 0 | 0 | 0 | 0 |
| Acetol | 0 | 0 | 1.5 | 1.6 | 1.7 |

Table 3 summarizes the performance of a copper chromium catalyst in the presence of 20 percent of water. The reactions were conducted at the following initial conditions: 5% wt of catalyst, and a hydrogen overpressure of 1400 kPa. The following table presents compositions after reacting in a closed reactor (with topping off of hydrogen) for 24 hours at a reaction temperature of 200° C.

TABLE 3

Summary of copper chromium catalyst performance based on 80 grams initial loading of glycerol and 20 grams of water.

|  | Initial Loading (g) | Best Possible (g) | Catalyst Copper Chromium (g) |
| --- | --- | --- | --- |
| Glycerol | 80 | 0 | 33.1 |
| Propylene glycol | 0 | 66.1 | 44.8 |
| Ethylene Glycol | 0 | 0 | 0 |
| Acetol | 0 | 0 | 3.2 |

Table 4 summarizes the impact of initial water content in the reactants on formation of propylene glycol from glycerol. The reactions were conducted at the following initial conditions: 5% wt of catalyst, and a hydrogen overpressure of 1400 kPa. The catalyst was purchased from Sud-Chemie as a powder catalyst having 30 m$^2$/g surface area, 45% CuO, 47% $Cr_2O_3$, 3.5% $MnO_2$ and 2.7% BaO. The following table presents compositions after reacting in a closed reactor (with topping off of hydrogen) for 24 hours at a reaction temperature of 200° C.

TABLE 4

Summary of catalyst performances based on different initial loadings of glycerol in water.

| Water (wt %) | % Conversion | % Yield | % Selectivity |
|---|---|---|---|
| 80 | 33.5 | 21.7 | 64.8 |
| 40 | 48 | 28.5 | 59.4 |
| 20 | 54.8 | 46.6 | 85.0 |
| 10 | 58.8 | 47.2 | 80.3 |
| 0 | 69.1 | 49.7 | 71.9 |

The reaction was performed using a small scale reaction distillation system like that shown as process equipment 100 in FIG. 1 to process a reaction mixture including 46.5 grams of refined glycerol and 53.5 grams water. The catalyst was purchased from Sud-Chemie as a powder catalyst having 30 $m^2/g$ surface area, 45% CuO, 47% $Cr_2O_3$, 3.5% $MnO_2$ and 2.7% BaO. Table 5 summarizes performance with higher initial water content using a small reaction distillation system.

TABLE 5

Example of reaction distillation.

| | Reactor | Distillate |
|---|---|---|
| Glycerol | 21.6 grams | 2.2 |
| Propane Diol | 6.4 | 9.5 |
| Ethylene Glycol | 0 | 0 |
| Acetol | 1.4 | 1.4 |

Use of Glycerol from Fatty Acid Glyceride Refinery

One preferred source of the polyhydric feedstock 104 is crude natural glycerol byproducts or intermediates, for example, as may be obtained from processes that make or refine fatty acid glycerides from bio-renewable resources. These are particularly preferred feedstocks for making an antifreeze mixture. When using these feedstocks, the antifreeze mixture is prepared as explained above by hydrogenation of glycerol over a catalyst, which is preferably a heterogeneous catalyst. The reactor-separator 102 may, for example, be a packed bed reactor, slurry, stirred or fluidized bed reactor. When the hydrogenation reaction is performed in a packed-bed reactor, the reactor effluent is largely free of catalyst. In the case of a slurry reactor, a heterogeneous catalyst may be filtered from the reactor effluent. The reactor-separator 102 may be used for slurry reactions by circulating hydrogen from the top vapor phase to the bottom of the reactor to create increased agitation and by preferably using a catalyst that has a density similar to the density of the liquid in the reactor. A fluidized bed may be used where the densities differ, where a catalyst bed is fluidized by the incoming hydrogen from line 108. Conventional agitation may also promote hydrogen contact in the liquid.

To make antifreeze, the process conditions need only provide moderate hydrogenation conversions of glycerol, e.g., those ranging from 60% to 90% conversion. This is because from 0% to 40% of the glycerol in the polyhydric feedstock 104 on a water-free basis may remain with propylene glycol products in the antifreeze product. For some product applications, the final antifreeze product may suitably contain up to 60% glycerol. Furthermore, when the product 118 contains a low glycerol concentration, e.g., less than 40% where there is an effective conversion of 60% to 90%, other known antifreezes may be mixed with the products 118. Alternatively, the purge materials 122 may be mixed with the contents of condensate tank 114, for example, after filtering, to form a salable product that may be directly discharged from the process equipment 100.

One particularly preferred source of polyhydric feedstock 104 for the reaction is the natural glycerol byproduct that is produced during the value-added processing of naturally occurring renewable fats and oils. For example, the glycerol byproduct may be a vegetable oil derivative, such as a soy oil derivative. This variety of polyhydric feedstock 104 may contain water, soluble catalysts, and other organic matter that are present in intermediate mixtures which are produced in the manufacture of glycerol for sale into the glycerol market. One advantage of the present instrumentalities is that little or no refining of these intermediates are necessary for their use as polyhydric feedstock 104 in making commercial antifreeze or deicing mixtures.

These intermediates and other polyhydric feedstocks 104 may contain high amounts of water. The ability to use polyhydric feedstocks 104 that contain high amounts of water advantageously reduces costs for this process over other uses for the glycerol. The water content both in the polyhydric feedstock 104 prior to the reaction and in the salable reaction product is generally between 0 and 50%.

The polyhydric feedstock 104 may contain residual catalyst that was added during alcoholysis of these intermediates. The fate of soluble residual catalysts, i.e., those that remain from alcoholysis in the polyhydric feedstock 104 and which are in the purge material 122 depends upon:
1. the specific type of soluble residual catalyst, and
2. any interaction between the residual catalyst and another catalyst that is added to the crude glycerol to promote hydrogenation within reactor-separator 102.

The residual catalyst content in the glycerol feedstock 104 from the processing of bio-renewable fats and oils is commonly between 0% and 4% or even up to 10% by weight on a water-free basis. One way to reduce the residual catalyst content is to minimize the amount that is initially used in alcoholysis of the fatty acid glyceride. The alcoholysis may, for example, be acid-catalyzed. Neutralizing the residual catalyst with an appropriate counter-ion to create a salt species that is compatible with the antifreeze specifications is preferred to removing the residual catalyst.

Alternatively, neutralization can be performed to precipitate the catalyst from the liquid glycerol. Calcium-containing base or salt may be used to neutralize the residual catalyst in the polyhydric feedstock 104, and the solid salts generated from this neutralization may be separated from the liquid, for example, by filtration or centrifugation of effluent from reactor-separator 102, such as by filtering purge material 122. Acid-base neutralization to form soluble or insoluble salts is also an acceptable method of facilitating separation. Specifically, neutralizing potassium hydroxide with sulfuric acid to form the dibasic salt is an acceptable procedure. As shown by way of example in FIG. 1, neutralization of sodium or potassium catalyst, which is sometimes introduced into the value-added processing method for fats and oils, can be achieved by adding stoichiometric equivalent amounts of a neutralizing agent 126, such as calcium oxide and/or sulfuric acid, to form the calcium salt of the catalyst. These salts are largely insoluble and may be filtered from the purge material 122. To improve separation of the substantially insoluble salt, the water content is preferably reduced to less than 20% by weight and the filtration is preferably performed at temperatures less than 40° C. and more preferably below 30° C. The optimal filtration temperature depends upon composition where the reduced solubility of salts at lower temperatures is weighed against lower viscosities at higher temperatures to identify the best filtration conditions.

One general embodiment for processing of crude glycerol to antifreeze in the fatty acid glyceride refinery embodiment follows a $C_1$ to $C_4$ alkyl alcohol alcoholysis process. The incoming crude glycerol feedstock 104 is neutralized by the addition of a neutralizing agent 126 to achieve a pH between 5 and 12, which is more preferably a pH between 5 and 9. The $C_1$ to $C_4$ alcohol and water are separated by distillation from the crude glycerol, such that the combined concentrations of water and $C_1$ to $C_4$ alcohols within reactor-separator 102 are less than 20 wt % by weight and, preferably, less than 5% by weight. In a stepwise process where the polyhydric feedstock 104 is added to the reactor-separator 104 at periodic intervals, selected components of these alcohols and/or their reaction products may be isolated by fractional distillation through overhead line 110 and discharged from condensate tank 114. This may be done by flash liberation of such alcohols at suitable times to avoid or limit their combining with propanediols, according to the principle of fractional distillation. Subsequent hydrogenation of the flashed glycerol within reactor-separator 102 suitably occurs by contacting the crude glycerol with a hydrogenation catalyst and hydrogen at a pressure ranging from 1 bar to 200 bar and at a temperature ranging from 100° to 290° C. until a conversion of the glycerol between 60% and 90% is achieved. More preferably, process conditions entail the contact pressure for hydrogenation ranging from 1 to 20 bar.

Separating the $C_1$ to $C_4$ alcohol and water is preferably achieved by selective flash separation at temperatures greater than 60° C. and less than 300° C. Alternatively, separating the $C_1$ to $C_4$ alcohol and water may be achieved in a process based on thermal diffusion, as is described in related application Ser. No. 10/420,047, where for example the reactor-separator 102 is a thermal diffusion reactor. Alternatively, water is added prior to hydrogenation as water promotes hydrogenation in the presence of certain catalysts.

The amount of organic matter in the polyhydric feedstock is substantially dependent upon the fat or oil from which the glycerol was obtained. The organic matter (other than glycerol) is typically fatty acid derivatives. One method for mitigating residual organic matter is by filtration. Alternatively, it is possible to decant insoluble organics from the glycerol in a gravity separator (not shown) at temperatures between 25 and 150° C. As necessary, the flash point of the mixture is preferably increased to greater than 100° C. by flash separation of volatiles from the glycerol-water mixture. Specifically, the residual $C_1$ to $C_4$ alkyl alcohol content in the feedstock is flash liberated to achieve feedstock concentrations that are preferably less than 1% alkyl alcohol. Depending upon the alkyl alcohol, vacuum may need to be applied to reach achieve the 1% alkyl alcohol concentration.

The following are preferred reaction conditions for conversion for use in processing these feedstocks. These are similar but not exactly the same as preferred +conditions that have been previously described for use in the reactor-separator 102. The reaction temperature is 150° C. to 250° C. The reaction time is from 4 to 28 hours. Heterogeneous catalysts are used which are known to be effective for hydrogenation, such as palladium, nickel, ruthenium, copper, copper zinc, copper chromium and others known in the art. Reaction pressure is from 1 to 20 bar, but higher pressures also work. Water in the polyhydric feedstock is preferably from 0% to 50% by weight, and more preferably from 5 to 15% water by weight.

The preferred reaction conditions provide a number of performance advantages. Operating at temperatures less than 250° C. dramatically reduces the amount of unintended by-product formation, for example, where lower concentrations of water may be used without formation of polymers or oligomers. Furthermore, operation at temperatures near 200° C., as compared to near 300° C., provides an increased relative volatility of propylene glycol that facilitates an improved separation of propylene glycol from the glycerol reaction mixture. The use of lower pressures allows the use of less expensive reaction vessels, for example, as compared to high-pressure vessels that operate above about 28 atmospheres or bar, while also permitting the propylene glycol to distill from solution at these temperatures. Even so, some embodiments are not limited to use at pressures less than 20 bars, and may in fact be practiced at very high hydrogen pressures. The disclosed process conditions are viable at lower pressures (less than 20 bar) whereas most other processes to produce similar products require much higher pressures.

By these instrumentalities, glycerol may also be hydrogenolysed to 1,2 and 1,3 propanediols. The 1,3 propanediol may be optionally separated from this mixture by methods known in the science and used as a monomer while the remaining glycerol and propanediols are preferably used as antifreeze.

Composition of Antifreeze Product from Glycerol of Biodiesel Facility

Biodiesel is one type of product that can be produced from a fatty acid glycerin refinery. After a conventional biodiesel methanolysis reaction, the methoxylation catalyst is preferably removed by filtration from a slurry reaction system. Other methods, such as centrifugation or precipitation, may be used to remove soluble catalysts from the glycerol byproduct of the biodiesel methanolysis reaction process. These processes are compatible with either batch or continuous operation. Methods known in the art may be used to convert the batch process procedures (described herein) to flow process procedures. Hydrogenation of the glycerol is performed to prepare a glycerol byproduct that preferably contains, on a water-free basis, from 0.5% to 60% glycerol, and 20% to 85% propylene glycol. More preferably, the glycerol byproduct contains on a water-free basis from 10% to 35% glycerol, and 40% to 75% propylene glycol. Also, as the preferred antifreeze of this invention is prepared from the crude natural glycerol byproduct of the $C_1$ to $C_4$ alkyl alcohol alcoholysis of a glyceride, the more preferable product also contains 0.2% to 10% C1 to C4 alkyl alcohol and 0 to 5% salt of the neutralized alcoholysis catalyst (more preferably 0.2 to 5% salt).

The glycerol conversion reactions have been observed to form a residue by-product. When this residue is soluble in the antifreeze product, the preferred application is to add it to the antifreeze product. The antifreeze may contain 1% to 15% of this residue by-product.

While the antifreeze products of this invention are commonly referred to as antifreeze, these same mixtures or variations thereof may be used as deicing fluids and anti-icing fluids.

When the reaction is run without hydrogen, acetol will form. This mixture can then subsequently (or in parallel) react in a packed-bed flow reactor in the presence hydrogen to be converted to propylene glycol. This process has the advantage that the larger reactor does not contain pressurized hydrogen.

The processes and procedures described in this text are generally applicable to refined glycerol as well as crude glycerol.

The catalyst used for most of the process development was a Sud-Chemie powder catalyst at 30 m$^2$/g surface area, 45% CuO, 47% $Cr_2O_3$, 3.5% $MnO_2$ and 2.7% BaO. Also used was a Sud-Chemie tablet catalyst at 49% CuO, 35% $Cr_2O_3$, 10%

SiO₂ and 6% BaO. Also used was a Sud-Chemie powder catalyst at 54% CuO and 45%.

EXAMPLE 3

Processing of Biodiesel Byproduct

Crude glycerol obtained as a by product of the biodiesel industry was used instead of refined glycerol. Biodiesel is produced using alcoholysis of bio-renewable fats and oils. The composition of feedstock 104 used in this example had an approximate composition as follows: glycerol (57%), methyl alcohol (23%), and other materials (soaps, residual salts, water) (20%). The above feedstock was reacted in the presence of hydrogen and catalyst to form a mixture containing propylene glycol. The reaction proceeded using 10 grams of the crude feedstock, 5% by weight of catalyst, and a hydrogen overpressure of 1400 kPa. The following Table 6 presents compositions after reacting in a closed reactor (with topping off of hydrogen) for 24 hours at a temperature of 200° C. The copper chromium catalyst used in this Example was reduced in presence of hydrogen at a temperature of 300° C. for 4 hours prior to the reaction.

TABLE 6

Summary of catalyst performances based on 10 grams of crude glycerol.

|  | Initial Loading (g) | Best Possible (g) | Final Product (g) |
| --- | --- | --- | --- |
| Crude Glycerol | 5.7 | 0 | 0.8 |
| Acetol | 0 | 0 | 0 |
| Propylene glycol | 0 | 4.6 | 3.1 |
| Water | 1 | 2.1 | 2.6 |

Reactive-Separation to Prepare Acetol and Other Alcohols

Figure 4:
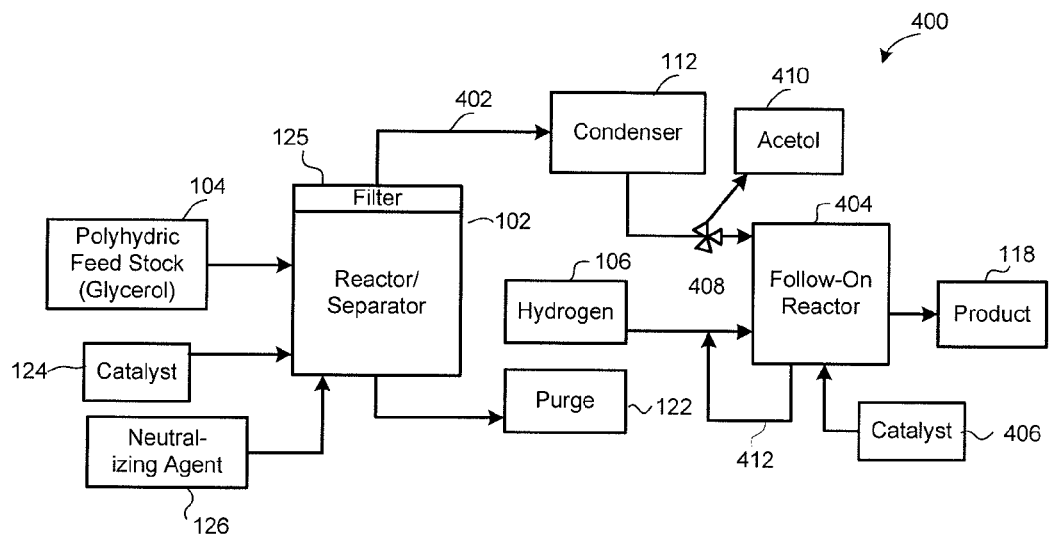
FIG. 4 is a schematic of the proposed reaction mechanism for conversion of acetol to propylene glycol via lactaldehyde intermediate.

As an alternative to reacting to form propylene glycol by use of the process equipment 100 shown in FIG. 1, FIG. 4 shows a modified version of the process equipment that has been previously described. Process equipment 400 is useful for forming acetol or other alcohols having boiling points less than about 200° C. Dehydration is the preferred reaction method, but cracking reactions may be used with feed stocks containing sugars or polysaccharides having carbon numbers greater than 3.

In general, the process equipment 400 is used for converting a three-carbon or greater sugar or polysaccharide to an alcohol dehydration product having a boiling point less than about 200° C. By way of example, a sugar or polysaccharide-containing feedstock with less than 50% by weight water is combined with a catalyst that is capable of dehydrating glycerol to form a reaction mixture. The reaction mixture is heated to a temperature ranging from 170° to 270° C. over a reaction time interval ranging from 0.5 to 24 hours at a pressure ranging from 0.2 to 25 bar.

The preferred reaction conditions for conversion of glycerol to form acetol include a process temperature ranging from 170° C. to 270° C., and this is more preferably from 180° C. to 240° C. The preferred reaction time ranges from 0.5 to 24 hours. Heterogeneous catalysts that are known to be effective for dehydration may be used, such as nickel, copper, zinc, copper chromium, activated alumina and others known in the art. The preferred reaction pressure ranges from 0.2 to 25 bar, and this is more preferably from the 0.5 to 3 bar. The feedstock may contain from 0% to 50% and more preferably 0 to 15% water by weight.

By these instrumentalities, glycerol may be dehydrated to acetol. Selective formation of acetol is documented for the copper-chromium catalyst by Examples 5 through 7 below. The same reaction conditions with different catalyst are effective for forming other alcohol products where the products have fewer alcohol functional groups than do the reagents. Fractional isolation of intermediates through reactive-distillation is particularly effective to increase yields and the embodiments is inclusive of processes to produce a range of products including but not limited to 1,3 propanediol and acrolein.

FIG. 4 shows process equipment 400 for the selective conversion of glycol to acetol. In FIG. 4, identical numbering is used for the same components that have been previously described with respect to FIG. 1. The reactor separator 102 as shown in FIG. 4 functions as a dehydration reactor. The polyhydric feedstock 104 and catalyst 124 enter reactor-separator 102 for a reaction that is limited to the dehydration step 204 of FIG. 2 by the absence of hydrogen, and in consequence the hydrogenation step 208 does not occur at this time. The dominant reaction product is acetol 202. Volatile fractions including acetol vapor exit the reactor-separator 102 through an overhead intermediate line 402 and liquefy in condenser 112. A follow-on reactor 404 functions as a hydrogenolysis reactor that accepts acetol and other liquids from condenser 112, and contacts the acetol with hydrogen to form propylene glycol as product 118. The catalyst 406 may be the same as or different from catalyst 126. The condenser 112 preferably operates at a temperature ranging from 25° C. to 150° C. and this is more-preferably from 25° C. to 60° C. It will be appreciated that the condenser 112 may be eliminated or positioned downstream of the follow-on reactor 404 if the follow-on reactor 404 operates as a vapor phase reactor.

When the process equipment 400 is operating in mode of producing propylene glycol product 118, a hydrogen recycle loop 412 recycles excess hydrogen from the follow-on reactor 404. This step preferably recycles unused hydrogen from the condenser back to the subsequent step reaction mixture. The reaction time of this subsequent step reaction ranges from 0.2 to 24 hours and more-preferably ranges from 1 to 6 hours.

The acetol that is delivered through intermediate line 402 to condenser 112 is optimally diverted through three way valve 408 to provide an acetol product 410.

EXAMPLE 4

Stepwise Production of Acetol then Propylene Glycol

Glycerol was reacted in the presence of copper chromium catalyst in two steps to form a mixture containing propylene glycol. In Step 1, relatively pure acetol was isolated from glycerol in absence of hydrogen at a reaction pressure of 98 kPa (vac). In Step 2, the acetol from Step 1 was further reacted in presence of hydrogen to propylene glycol at 1400 kPa hydrogen over pressure using similar catalyst that is used for the formation of acetol. The catalyst used in the step 1 of this Example is used in the condition in which they arrived and the catalyst used in the Step 2 was reduced in presence of hydrogen at a temperature of 300° C. for 4 hours prior to the reaction.

The following tables present composition of the final product in Step 1 and Step 2

TABLE 7

Example reaction conditions for converting glycerol to propylene glycol.

|  | Initial Loading (g) | Best Possible (g) | Final Product (g) |
|---|---|---|---|
| Step 1: Formation and isolation of acetol intermediate from glycerol using copper-chromite catalyst. Catalyst—5% unreduced powder Cu/Cr, Reaction time—1.5 hr at 220° C. and 3 hr at 240° C., Reaction Pressure—98 kPa (vac). | | | |
| Glycerol | 36.8 | 0 | 3.6 |
| Acetol | 0 | 29.6 | 23.7 |
| Propylene glycol | 0 | 0 | 1.7 |
| Water | 0 | 7.2 | 6.9 |
| Step 2: Formation of propylene glycol from acetol intermediate from Step 1 using same catalyst. Catalyst—5% reduced powder Cu/Cr, Reaction time—12 hr, Reaction Temperature—190° C., Reaction Pressure—1400 kPa. | | | |
| Glycerol | 0 | 0 | 0 |
| Acetol | 4.5 | 0 | 0 |
| Propylene glycol | 0 | 4.6 | 4.3 |

EXAMPLE 5

Batch Versus Semi Batch Processing

Glycerol was reacted in presence of copper chromium catalyst to form acetol by each of two process modes: batch and semi batch. Relatively pure acetol was isolated from glycerol in absence of hydrogen at a reaction pressure of 98 kPa (vac). In this reaction 92 grams of glycerol would form a maximum of 74 grams acetol at the theoretical maximum 100% yield. Either process mode produced a residue. When dried, the residue was a dark solid coated on the catalyst that was not soluble in water.

In semi-batch operation, the reactor was provisioned with catalyst and glycerol was fed into the reactor at a uniform rate over a period of about 1.25 hours. In batch operation, all of the glycerol and catalyst was loaded into the reactor at the start of the reaction. The following results show the semi-batch reactive-distillation has higher yields and selectivities than batch. The higher catalyst loading provided higher yields and selectivities. It was observed that the catalyst activity decreased with reaction time and the amount of residue increased with reaction time.

The copper chromium catalysts used in this Illustrative Example were used in the condition in which they arrived.

TABLE 8

Comparison of Semi-Batch (Continuous) Reactive-distillation and Batch Reactive-distillation. Formation and isolation of acetol intermediate from glycerol using copper-chromite catalyst. Catalyst—5% unreduced copper chromium powder Reaction conditions:

Reaction Pressure—98 kPa (vac)
Reaction temperature—240° C.
Reaction complete time—2 hr
Glycerol feed rate—33.33 g/hr for Semi-Batch Reactions
The following three reactions were conducted:

RXN 8.1—Semi-Batch reaction at 5% catalyst loading
RXN 8.2—Semi-Batch reaction at 2.5% catalyst loading
RXN 8.3—Batch reaction 5% catalyst loading The following are reaction details of RXN 8.1: Initial loading of glycerol, 54.29; Glycerol in Distillate, 4.91; Residue, 3.80; and Amount of glycerol reacted, 49.38 all in grams. The glycerol reacted as described in Table 9.

TABLE 9

Mass balance details on RXN 8.1. Catalyst loading was 5%.

|  | Reacted Glycerol (g) | Best possible (g) | Distillate (g) |
|---|---|---|---|
| Glycerol | 49.38 | 0 | 3.64 |
| Acetol | 0 | 39.71 | 35.99 |
| Propylene glycol | 0 | 0 | 1.65 |
| Water | 0 | 9.66 | 5.79 |

The following are reaction details of RXN 8.2: Initial loading of glycerol, 52.8; Glycerol in Distillate, 3.85; Residue, 4.91; and Amount of glycerol reacted, 48.95 all in grams. The glycerol reacted as described in Table 10.

TABLE 10

Mass balance details on RXN 8.2. Catalyst loading was 2.5%.

|  | Reacted Glycerol (g) | Best possible (g) | Distillate (g) |
|---|---|---|---|
| Glycerol | 48.95 | 0 | 3.85 |
| Acetol | 0 | 39.37 | 33.51 |
| Propylene glycol | 0 | 0 | 1.63 |
| water | 0 | 9.58 | 6.24 |

The following are reaction details of RXN 8.2: Initial loading of glycerol, 42.48; Glycerol in Distillate, 3.64; Residue, 5.68; and Amount of glycerol reacted, 33.16 all in grams. The glycerol reacted as described in Table 11.

TABLE 11

Mass balance details on RXN 8.3. Catalyst loading was 5%.

|  | Reacted Glycerol (g) | Best possible (g) | Distillate (g) |
|---|---|---|---|
| Glycerol | 36.80 | 0 | 3.64 |
| Acetol | 0 | 29.60 | 23.73 |
| Propylene glycol | 0 | 0 | 1.67 |
| water | 0 | 7.2 | 6.99 |

As reported in the following examples, various studies were performed to assess the ability to control the residue problem.

EXAMPLE 6

Control of Residue by Water Content of Feedstock

Glycerol was reacted in presence of copper chromium catalyst to form acetol at conditions similar to Illustrative Example 4 with 2.5% catalyst loading and in a semi-batch reactor method. Water was added to the glycerol to evaluate if water would decrease the accumulation of the water-insoluble residue. Table 12 summarizes the conversion results. These data illustrate that a small amount of water reduces the tendency for residue to form. The copper chromium catalyst used in this Illustrative Example was used in the condition in which they arrived.

TABLE 12

Impact of water on residue formation.

| Water (wt %) | Initial Glycerol (g) | Glycerol in Distillate (g) | Best Possible of Acetol (g) | Acetol in Distillate (g) | Residue (g) | Conversion (%) | Residue: Initial Glycerol Ratio |
|---|---|---|---|---|---|---|---|
| 0% | 52.8 | 3.85 | 39.37 | 33.51 | 4.91 | 92.71% | 9.30% |
| 5% | 53.26 | 4.93 | 38.87 | 35.23 | 3.47 | 90.74% | 7.02% |
| 10% | 56.25 | 8.55 | 38.36 | 34.48 | 3.45 | 84.80% | 6.13% |
| 20% | 55.52 | 9.67 | 36.87 | 33.13 | 2.95 | 82.58% | 5.31% |

Catalyst - 2.5% unreduced powder Cu/Cr
Reaction Pressure - 98 kPa (vac)
Reaction temperature - 240° C.
Reaction complete time - 2 hr
Glycerol feed rate - 33.33 g/hr

EXAMPLE 7

Control of Residue by Catalyst Loading

Glycerol was reacted in presence of copper chromium catalyst to form acetol in a semi-batch reactor method. The impact of lowering catalyst loadings was evaluated to determine the impact of catalyst loading on acetol yield and residue formation. Table 13 summarizes the conversion results. These data illustrate that the formation of residue may be autocatalytic—it increases more than linearly with increasing throughput of glycerol over the catalyst. Also, the selectivity decreases with increasing throughput of glycerol over a fixed catalyst loading in the reactor.

The copper chromium catalyst used in this Illustrative Example was used in the condition in which they arrived.

TABLE 13

Impact of catalyst to glycerol throughput ratio on residue formation.

| Reaction | Catalyst % | Total feed of Glycerol (g) | Residue (g) | Conversion (%) | Acetol Selectivity | Residue: Reacted-Glycerol Ratio |
|---|---|---|---|---|---|---|
| 1 | 5% | 27.15 | 1.9 | 90.96% | 90.62% | 7.70% |
| 2 | 2.50% | 52.80 | 4.91 | 92.71% | 85.11% | 10.03% |
| 3 | 1.67% | 77.22 | 7.54 | 90.44% | 76.94% | 10.76% |
| 4 | 1.25% | 105.68 | 11.7 | 89.23% | 73.50% | 12.11% |
| 5 | 0.83% | 151.69 | 17.18 | 86.87% | 59.76% | 13.03% |

Catalyst - 1.25 g unreduced powder Cu/Cr
Reaction Pressure - 98 kPa (vac)
Reaction temperature - 240° C.
Glycerol feed rate - 33.33 g/hr

EXAMPLE 8

Regeneration of Catalyst

This example illustrates the stability of the copper chromium catalyst for the formation of propyelene glycol from acetol. The following were the approximate initial conditions: 4.5 grams of acetol, 2 wt % of catalyst, and a hydrogen overpressure of 1400 kPa. The following table presents compositions after reacting in a closed reactor (with topping off of hydrogen) for 4 hours at a reaction temperature of 185° C. The copper chromium catalyst was reduced in presence of hydrogen at a temperature of 300° C. for 4 hours prior to the reaction. The catalyst after each run was filtered from the reaction products, washed with methanol and then dried in a furnace at temperature of 80° C. This regenerated catalyst was reused in the subsequent reactions. Similar regeneration procedure is repeated 10 times and the results are summarized in Table 14. These data illustrate the ability to reuse catalyst for the hydrogenation of acetol.

The copper chromium catalyst used in this Illustrative Example was reduced in presence of hydrogen at a temperature of 300° C. for 4 hours prior to the reaction.

TABLE 14

Summary of catalyst performances based on 4.5 grams of acetol.

| | Acetol (g) | Propylene glycol (g) | Lactaldehyde (g) |
|---|---|---|---|
| initial | 4.5 | 0 | 0 |
| Run 1 | 0.5 | 3.62 | 0.51 |
| Run 2 | 0.29 | 3.85 | 0.56 |

TABLE 14-continued

Summary of catalyst performances based on 4.5 grams of acetol.

| | Acetol (g) | Propylene glycol (g) | Lactaldehyde (g) |
|---|---|---|---|
| Run 3 | 0.19 | 4.19 | 0.53 |
| Run 4 | 0.07 | 4.41 | 0.47 |
| Run 5 | 0.05 | 4.42 | 0.49 |
| Run 6 | 0.05 | 4.39 | 0.51 |
| Run 7 | 0 | 4.41 | 0.36 |
| Run 8 | 0.24 | 4.2 | 0.42 |
| Run 9 | 0.27 | 4.2 | 0.43 |
| Run 10 | 0.21 | 4.11 | 0.4 |

EXAMPLE 9

Ability to Reuse Catalyst of Acetol-Forming Reaction

This example illustrates that a powder catalysts may be treated or reactivated by hydrogen treatment, but also that one powder catalyst that contains 54% CuO and 45% $Cr_2O_3$ has better reuse properties than does another powder catalyst at 30 $m^2$/g surface area, 45% CuO, 47% $Cr_2O_3$, 3.5% $MnO_2$ and 2.7% BaO. For the powder catalyst at 54% CuO and 45% $Cr_2O_3$, the data of Table 15 demonstrate that residue formation rate is similar to that of the powder catalyst at 30 $m^2$/g surface area, 45% CuO, 47% $Cr_2O_3$, 3.5% $MnO_2$ and 2.7% BaO (Table 14). The data of Table 16 demonstrate the 54% CuO and 45% $Cr_2O_3$ catalyst can be used repeatedly (at laboratory scale, 1-3% of the catalyst was not recovered from reaction to reaction). The data of Table 17 demonstrate that reuse is more difficult with the 45% CuO, 47% $Cr_2O_3$, 3.5% $MnO_2$ and 2.7% BaO Catalyst.

TABLE 15

Impact of catalyst to glycerol throughput ratio on residue formation. The catalyst in this table is a powder catalyst at 54% CuO and 45% $Cr_2O_3$. This compares to the catalyst of Table 13 which is a powder catalyst at 30 $m^2$/g surface area, 45% CuO, 47% $Cr_2O_3$, 3.5% $MnO_2$ and 2.7% BaO. Reactions were semi-batch.

| Reaction | Catalyst (%) | Total feed of Glycerol (g) | Residue (g) | Conversion (%) | Acetol Selectivity (%) | [Residue]: [Reacted-Glycerol] Ratio |
|---|---|---|---|---|---|---|
| 1 | 5% | 26.35 | 1.95 | 89.82% | 87.05% | 8.36% |
| 2 | 2.50% | 53.38 | 5.41 | 91.05% | 82.01% | 11.13% |
| 3 | 1.25% | 102.98 | 12.36 | 89.07% | 78.86% | 13.47% |

Catalyst - 1.25 g unreduced Cu/Cr, powder catalyst at 54% CuO and 45% Cr2O3.
Pressure - 98 kPa (vac); Temperature - 240° C.; Glycerol feed rate - 33.33 g/hr

TABLE 16

Impact of reuse on powder catalyst at 54% CuO and 45%. Catalyst is loaded at 5% and is unreduced.
Catalyst—2.5 g unreduced Cu/Cr, powder catalyst at 54% CuO and 45% $Cr_2O_3$.
Pressure—98 kPa (vac); Temperature—240° C.;
Glycerol feed rate—33.33 g/hr

| | Total feed of Glycerol (g) | Residue (g) | Conversion (%) | Acetol Selectivity (%) | Residue: Initial-Glycerol Ratio |
|---|---|---|---|---|---|
| Fresh | 52.77 | 3.96 | 89.82% | 87.05% | 7.51% |
| Reused 1 | 52.16 | 4.11 | 91.28% | 88.52% | 7.88% |
| Reused 2 | 51.72 | 3.89 | 91.74% | 88.56% | 7.53% |
| Reused 3 | Catalysts still could be recovered | | | | |

TABLE 17

Impact of reuse on powder catalyst at 30 $m^2$/g surface area, 45% CuO, 47% $Cr_2O_3$, 3.5% $MnO_2$ and 2.7% BaO.
Catalyst—2.5 g unreduced powder Cu/Cr
Pressure—98 kPa (vac); Temperature—240° C.;
Glycerol feed rate—33.33 g/hr

| | Total feed of Glycerol (g) | Residue (g) | Conversion (%) | Acetol Selectivity (%) | Residue: Initial-Glycerol Ratio |
|---|---|---|---|---|---|
| Fresh | 54.29 | 3.80 | 90.95% | 90.62% | 7.01% |
| Reused 1 | 53.13 | 3.99 | 88.92% | 88.80% | 7.51% |
| Reused 2 | Catalyst could not be recovered—residue was totally solidified | | | | |

The two catalysts at initial condition performed about the same for the acetol forming reaction; however, the 45% CuO, 47% $Cr_2O_3$, 3.5% $MnO_2$ and 2.7% BaO catalyst at a loading of lesser than 5% formed a different type of residue that was more resistant to catalyst recovery. For both catalysts, it was generally observed that as reactions proceeded, the reaction rates tended to reduce. At the end of the semi-batch reaction a digestion of the mixture was induced by stopping the feed and allowing the reaction to proceed for about 30 min to an hour—during this digestion the volume of the reaction mixture decreased and the residue became more apparent.

For the 54% CuO and 45% $Cr_2O_3$ catalyst, the residue tends to be stable. This residue takes a solid form in room temperature and a slurry form at the reaction temperature during the long period of reaction time. A methanol wash readily removed the residue, allowing the catalyst to be reused multiple times. The solid was soft and tacky in nature and readily dissolved in methanol to form slurry. The catalyst was washed with methanol until the wash was clear and then the catalyst was dried in a furnace at 80° C. to remove the methanol. The physical appearance of this catalyst after washing was similar to that of the new catalyst.

In the case of 45% CuO, 47% $Cr_2O_3$, 3.5% $MnO_2$ and 2.7% BaO catalyst the residue was, however, different. In the case of 5% catalyst loading, residue started foaming on the catalyst at 30 min after total glycerin was fed, i.e., 30 minutes into the reaction. Once foaming started, a methanol wash was not effective for removing the residue from the catalyst. If the reaction was stopped prior to commencement of foaming, the methanol was effective in removing the residue from the catalyst. When catalyst loading less than 2.5%, the residue started foaming while the glycerin was still being fed to the reactor, and the catalyst could not be recovered at end of the reaction. The 54% CuO and 45% $Cr_2O_3$ catalyst produced a residue that is a solid at room temperature.

These trends in reuse of catalyst are applicable to conditions for conversion of glycerin to acetol as well as the "single-pot" conversion of glycerin to propylene glycol.

EXAMPLE 10

Lactaldehyde Mechanism

Acetol was hydrogenated in presence of copper chromium catalyst to form a mixture containing propylene glycol. The following were the approximate initial conditions: 10 grams of acetol, 2 wt % of catalyst, and a hydrogen overpressure of 1400 kPa. The following table presents compositions after reacting in a closed reactor (with topping off of hydrogen) for 4 hours at a reaction temperature of 190° C. Table 18 shows the effect of reaction temperature on the formation of propylene glycol from acetol. The data illustrate that good conversions are attainable at 190° C. The data illustrate that the co-product (likely undesirable) of lactaldehyde is produced at lower selectivities at temperatures greater than 150° C. Optimal temperatures appear to be 190° C. or higher. The copper chromium catalyst used in this Illustrative Example was reduced in presence of hydrogen at a temperature of 300° C. for 4 hours prior to the reaction.

TABLE 18

Summary of catalyst performances based on 9 grams of acetol. The pressure is 1400 kPa with a 5% catalyst loading.

| Temperature C. | Acetol (g) | Propylene glycol (g) | Lactaldehyde (g) |
| --- | --- | --- | --- |
| Unreacted | 10 | 0 | 0 |
| 50 | 8.25 | 1.86 | 0.13 |
| 100 | 5.74 | 3.93 | 0.47 |
| 150 | 3.10 | 4.31 | 2.82 |
| 180 | 1.64 | 7.90 | 0.89 |
| 190 | 0.56 | 9.17 | 0.58 |

Table 19 shows the effect of initial water content in the reactants on the formation of propylene glycol from acetol. The data illustrate that water can improve yields to propylene glycol. Selectivity to propylene glycol decreases as the reaction goes beyond 10-12 hrs.

TABLE 19

Summary of catalyst performances based on different initial loadings of water. The reaction temperature is 190° C., at a pressure of 1400 kPa, a 5% catalyst loading and a reaction time of 24 hours. The total loading of water with acetol is 10 grams.

| Water (% wt) | Acetol (g) | Propylene glycol (g) | Lactaldehyde (g) |
| --- | --- | --- | --- |
| 10 | 0.47 | 7.65 | 0 |
| 20 | 0.22 | 5.98 | 0.7 |
| 50 | 0.22 | 4.35 | 0.27 |

Table 20 shows the effect of initial catalyst concentration on the formation of propylene glycol from acetol. The data illustrate that the highest yields are attained at the higher catalyst loadings.

TABLE 20

Summary of catalyst performances based on 4.5 grams of acetol. The reaction temperature is 190° C., at a pressure of 1400 kPa, and no added water.

| Catalyst Concentration (wt %) | Reaction Time (h) | Acetol (g) | Propylene glycol (g) | Lactaldehyde (g) |
| --- | --- | --- | --- | --- |
| Initial | — | 4.5 | 0 | 0 |
| 5% | 4 | 0.29 | 4.46 | 0.22 |
| 2% | 4 | 0.14 | 4.27 | 0.2 |
| 1% | 4 | 1.32 | 3.45 | 0.29 |
| 0.5% | 4 | 1.56 | 3.14 | 0.32 |
| 1% | 6 | 0.58 | 3.78 | 0.25 |
| 0.5% | 6 | 1.27 | 3.29 | 0.33 |

Reactive-Separation with Gas Stripping

The use of the reactor-separator 102 is very effective for converting glycerol to acetol as illustrated by the foregoing Examples. These examples illustrate, for example, the effective use of water and catalyst loading to reduce formation of residue. Two disadvantages of the reactions were the formation of residual and operation at small amounts of vacuum.

The most preferred approach overcomes the vacuum operation by using a gas to strip the acetol from solution. Thus, the process equipment operates at a more optimal pressure, such as slightly over atmospheric pressure, to make advantageous use of fugacity (partial pressures) for the selective removal of vapor from the reaction mixture. The stripper gases may be inert gases such as nitrogen to strip out the acetol. Steam may also be used to strip out the acetol. The most-preferred stripping gas is hydrogen.

Use of hydrogen at pressures slightly above atmospheric pressure strips the acetol and/or propylene glycol from solution as they are formed. In addition, the preferred hydrogen stripper gas keeps the catalyst reduced and provides reaction paths that prevent residue formation and/or react with the residue to form smaller molecules that also strip from solution. The reactions that strip the residue may include use of additional catalysts that are known to be effective for catalytic cracking, and the use of such stripper gas in combination with catalytic cracking catalysts is referred to herein as a strip-crack process. The hydrogen is preferably either recycled in the reactor or compressed with the acetol for a second reaction at higher pressure.

The preferred reaction process includes a first reactor. In the first reactor, the first product and alternative product are removed as vapor effluents from a liquid reaction where a sufficient hydrogen pressure is present to reduce the residue formation by at least 50% as compared to the residue formation rate without hydrogen present. The preferred hydrogen partial pressures are between 0.2 and 50 bars, more preferably between 0.5 and 30 bars, and most preferably between 0.8 and 5 bars.

To achieve higher conversions to the alternative product, the first product may be reacted in a second reactor that is operated at higher partial pressures of hydrogen. In the second reactor, the partial pressure of hydrogen is at least twice the partial pressure of hydrogen in the second reactor, more preferably the partial pressure of hydrogen is at least four times the partial pressure of hydrogen in the first reactor.

The respective temperatures of the first and second reactors are preferably above the normal boiling point of the first product.

The use of hydrogen has an additional advantage of reducing residue that tends to deactivate catalysts which are useful in the disclosed process. In this sense, the hydrogen may be used as the gas purge or stripper gas, as well as a reagent in the first reactor. For example, in the cracking of petroleum to gasoline, it is well-known that hydrogen reduces the formation of residue that tends to deactivate of the catalyst; however, the use of hydrogen is more expensive than cracking of petroleum in the absence of hydrogen. In petroleum industry practice, considerable catalytic cracking is performed in the absence of hydrogen with product loss, and specialized equipment is devoted to regenerating the deactivated catalyst. Those other practices differ from the presently disclosed use of hydrogen stripper gas that is sufficient to reduce catalyst deactivation, but is sufficiently low in amount and amount/pressure to allow the non-hydrogen cat-cracking to dominate, e.g., at a pressure less that 50 bars, while the reaction is underway.

Figure 5:
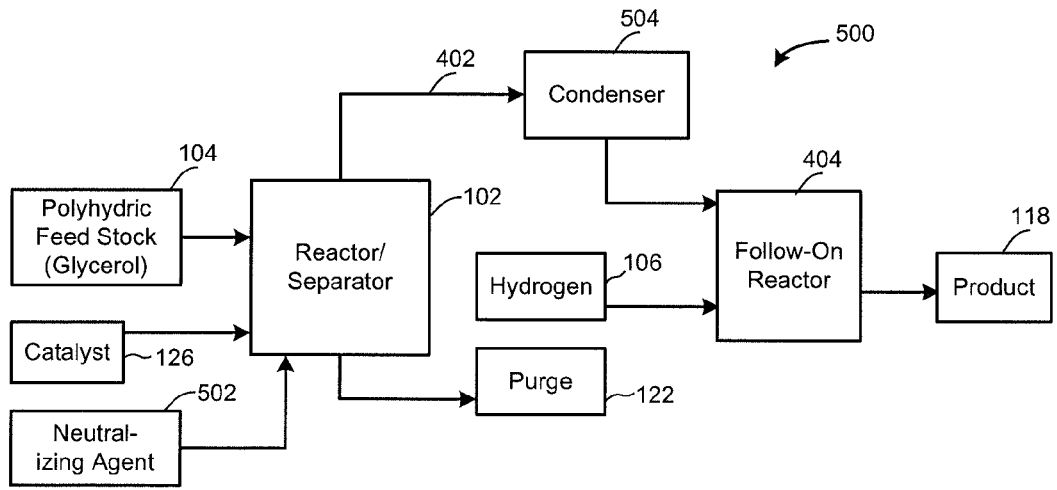
FIG. 5 is a schematic of the proposed two-step alternative embodiment for converting glycerol to acetol and then converting acetol to propylene glycol where hydrogen is used for the first reactor at a lower pressure and then the hydrogen is compressed for use in the second reactor.

FIG. 5 shows one embodiment that implements these concepts. Process equipment 500 the process where the hydrogen is compressed to proceed to the second reaction. In FIG. 5, like numbering is maintained with respect to identical elements as shown in FIG. 4. The reaction process proceeds as described with respect to FIG. 4, except low pressure hydrogen stripper gas 502 is applied to reactor separator 102, for example, at a pressure slightly above atmospheric pressure. Although some of this gas does result in the production of propylene glycol, the stripping of acetol is predominant. A mixture of acetol, propylene glycol and water vapor flows through overhead line 402 to compressor 504, which pressurizes the vapors to a suitably higher pressure for use in the follow-on reactor 404. The extant hydrogen is optionally supplemented by additional hydrogen 106 to establish the preferred reaction conditions discussed above.

Figure 6:
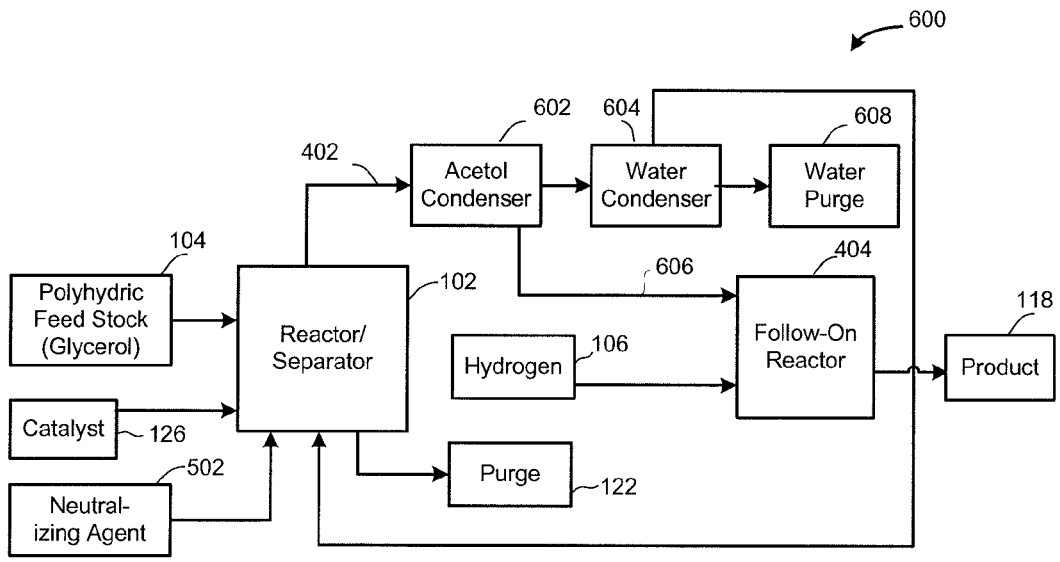
FIG. 6 is a schematic of the proposed two-step alternative embodiment for converting glycerol to acetol and then converting acetol to propylene glycol where hydrogen is used for the first reactor at a lower pressure and water is removed from the vapor effluents from the first reactor to allow purging of the water from the system.

FIG. 6 shows another embodiment, that of process equipment 600. In FIG. 6, like numbering is maintained with respect to identical elements as shown in FIG. 5. In process equipment 600, the effluent through intermediate overhead line 402 is applied to a series of condensers 602, 604 that decrease in their relative temperatures to condense first the acetol in acetol condenser 604 and then water in water condenser 604. The condensed acetol is applied to line 606, e.g., by pumping at the requisite pressure, for delivery to the follow-on reactor 404. Water effluent from water condenser 604 is discharged as water purge 608.

The hydrogen pressures (or partial pressures) for this process in the respective reactor vessels may be lower than is required for "good" hydro-cracking and/or hydrogenolysis but sufficient to stop catalyst deactivation.

In addition to reactor configurations, other methods known in the science for reducing residue (often an oligomer) formation is the use of a solvent. The solvent can reduce residue formation or dissolve the residue therein extending catalyst life. Solvents are preferably not reactive liquids. Supercritical solvents, such as carbon dioxide, have also been demonstrated as effective for extending catalyst life when residue formation otherwise coats the catalyst.

Applicability to Broader Reaction Mechanisms

The process that has been shown and described has been proven effective for production of acetol and propylene glycol, but is not limited to the reaction mechanisms of FIGS. 2 and 3. The process and process equipment is generally applicable to a range of reactions having similar overall mechanisms including at least four classes of such reactions in context of the discussion below.

A first class of liquid phase catalytic reaction occurs where a reactant (e.g. glycerol) distributes predominantly in a liquid phase and the reactant is converted to at least a first product (e.g. acetol) that that has a boiling point at least 20° C. lower in temperature than the reactant.

A second class of liquid phase catalytic reaction occurs where the reactant reacts in a parallel mechanism with hydrogen to form at least one alternative product (e.g. propylene glycol) where the alternative product has a boiling point that is at least 20° C. lower in temperature than the reactant. The selectivity to formation of the alternative produce(s) from this second reaction is greater than 0.5 when in the presence of hydrogen and hydrogen partial pressures in excess of 100 bars.

A third class of reaction proceeds substantially in parallel the first reaction including the reactant forming a higher molecular weight residue species that directly or indirectly reduces the effectiveness of the catalyst promoting the first reaction.

A fourth class of reaction that occurs when hydrogen is present that substantially inhibits the formation of the residue of the third reaction where the rate of formation of residue is reduced by at least 50% with the hydrogen partial pressure in 50 bars.

The process includes use in appropriate reactor configurations, such as the process equipment 100, 400, 500 and/or 600 discussed above.

Those skilled in the art will appreciate that the foregoing discussion teaches by way of example, not by limitation. The disclosed instrumentalities set forth preferred methods and materials, and may not be narrowly construed to impose undue limitations on the invention. The scope of the inventor's patentable inventions is defined by the claims, nothing else. Furthermore, the inventors hereby state their intention to rely upon the Doctrine of Equivalents to protect the full scope of their rights in what is claimed.

We claim:

1. A process for converting glycerol to propylene glycol with high selectivity, comprising the steps of:
   heating a glycerol-containing feedstock material in presence of a catalyst that is capable of dehydrating glycerol at a temperature from 170° C. to 270° C. and a pressure from 0.2 to 25 atmospheres with hydrogen as a limiting reagent to prevent formation of propylene glycol such that there is resultant formation of acetol in the feedstock material;
   liberating the acetol in vapor phase from the feedstock material; and
   reacting the acetol in vapor phase with hydrogen in the presence of a catalyst that is capable of hydrogenating acetol at a hydrogen partial pressure ranging from 0.2 to 50 bars to form propylene glycol.

2. The process of claim 1, wherein the glycerol-containing feedstock used in the step of heating contains from 5% to 15% water by weight.

3. The process of claim 1, wherein the catalyst used in the step of heating is a heterogeneous catalyst selected from the group consisting of palladium, nickel, rhodium, copper, zinc, chromium and combinations thereof.

4. The process of claim 1, wherein the step of liberating the acetol includes stripping the acetol by the action of a gas.

5. The process of claim 4, wherein the gas is primarily hydrogen.

6. The process of claim 5, wherein the temperature used in the heating step ranges from 180° C. to 220° C.

7. The process of claim 6, wherein the pressure used in the heating step ranges from 5 to 18 atmospheres.

8. The process of claim 5, wherein the step of condensing occurs using a condenser operating at a temperature ranging from 25° C. to 150° C.

9. The process of claim 7, wherein the condenser operates at a temperature ranging from 25° C. to 60° C.

10. The process of claim 6, comprising a step of adding a hydrogen co-reagent to promote conversion of acetol to propylene glycol.

11. The process of claim 10, comprising a step of recycling unused hydrogen from the condenser back to the reaction mixture.

12. The process of claim 1, wherein the reaction time of the heating step ranges from 4 to 46 hours.

13. The process of claim 1, wherein the reaction time of the heating step ranges from 4 to 28 hours.

* * * * *